(12) United States Patent
Hagenbuch et al.

(10) Patent No.: US 11,278,381 B2
(45) Date of Patent: Mar. 22, 2022

(54) MONOCHROMATIC DENTAL SHAPED ARTICLE AND BLANK FOR MAKING DENTAL RESTORATIONS

(71) Applicant: Ivoclar Vivadent AG, Schaan (LI)

(72) Inventors: Konrad Hagenbuch, Haag (CH); Harald Kerschbaumer, Klaus (AT); Konrad Gurschler, Schnals (IT); Clemens Andreas Häfele, Weiler (AT); Thomas Baaske, Mels (CH)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 16/487,360

(22) PCT Filed: Mar. 15, 2018

(86) PCT No.: PCT/EP2018/056542
§ 371 (c)(1),
(2) Date: Aug. 20, 2019

(87) PCT Pub. No.: WO2018/167213
PCT Pub. Date: Sep. 20, 2018

(65) Prior Publication Data
US 2020/0054423 A1 Feb. 20, 2020

(30) Foreign Application Priority Data
Mar. 17, 2017 (EP) .................. 17161722

(51) Int. Cl.
| A61C 13/08 | (2006.01) |
| A61C 13/087 | (2006.01) |
| A61C 13/09 | (2006.01) |
| A61C 13/083 | (2006.01) |
| A61C 13/00 | (2006.01) |
| A61K 6/00 | (2020.01) |
| A61K 6/887 | (2020.01) |
| A61K 6/78 | (2020.01) |

(52) U.S. Cl.
CPC ........ *A61C 13/082* (2013.01); *A61C 13/0004* (2013.01); *A61C 13/0022* (2013.01); *A61C 13/083* (2013.01); *A61C 13/087* (2013.01); *A61C 13/09* (2013.01); *A61K 6/78* (2020.01); *A61K 6/887* (2020.01); *A61C 2201/002* (2013.01)

(58) Field of Classification Search
None
See application file for complete search history.

(56) References Cited

U.S. PATENT DOCUMENTS

| 4,291,047 A | 9/1981 | Kranz et al. |
| 4,447,520 A | 5/1984 | Henne et al. |
| 4,737,593 A | 4/1988 | Ellrich et al. |
| 5,534,559 A | 7/1996 | Leppard et al. |
| 5,990,195 A | 11/1999 | Arita |

(Continued)

OTHER PUBLICATIONS

International Preliminary Report on Patentability of PCT/EP2018/056542, dated Mar. 15, 2018, 10 pages.

*Primary Examiner* — Tae H Yoon
(74) *Attorney, Agent, or Firm* — Ann M. Knab; Thad McMurray (57) ABSTRACT

Monochromatic dental shaped body, which has an opacity of from 70 to 78%, and a process for its production.

21 Claims, 1 Drawing Sheet

(56) References Cited

U.S. PATENT DOCUMENTS

| | | | |
|---|---|---|---|
| 6,196,843 B1* | 3/2001 | Kawaguchi | A61K 6/887 |
| | | | 433/212.1 |
| 7,932,304 B2* | 4/2011 | Moszner | A61K 6/836 |
| | | | 523/117 |
| 8,317,516 B2 | 11/2012 | Rusin et al. | |
| 9,044,292 B2* | 6/2015 | Velamakanni | A61C 13/0835 |
| 9,192,456 B2* | 11/2015 | Howe | A61C 13/081 |
| 9,554,971 B2* | 1/2017 | Xu | A61K 6/30 |
| 10,085,923 B2* | 10/2018 | Nakatsuka | A61C 13/087 |
| 2005/0154081 A1 | 7/2005 | Yin et al. | |
| 2007/0015110 A1* | 1/2007 | Zhang | A61C 8/0012 |
| | | | 433/173 |
| 2007/0232718 A1 | 10/2007 | Jia et al. | |
| 2008/0076847 A1 | 3/2008 | Moszner et al. | |
| 2010/0093886 A1* | 4/2010 | Fusejima | A61K 6/887 |
| | | | 523/116 |
| 2015/0305987 A1* | 10/2015 | Pflesser | A61K 6/891 |
| | | | 424/78.08 |
| 2016/0338806 A1* | 11/2016 | Nazzal | A61C 13/082 |
| 2017/0071712 A1* | 3/2017 | Karazivan | B33Y 30/00 |
| 2017/0224591 A1 | 8/2017 | Vogel et al. | |

* cited by examiner

MONOCHROMATIC DENTAL SHAPED ARTICLE AND BLANK FOR MAKING DENTAL RESTORATIONS

CROSS-REFERENCE TO RELATED APPLICATIONS

This application is a National Stage application of International patent application PCT/EP2018/056542 filed on Mar. 15, 2018, which claims priority to European patent application No. 17161722.8 filed on Mar. 17, 2017, the disclosures of which are incorporated herein by reference in their entirety.

FIELD OF THE INVENTION

The present invention relates to monochromatic shaped bodies, blanks and dental shaped parts, processes for the production thereof and the use thereof for the production of dental restoration shaped parts. The shaped bodies preferably consist of a filled or unfilled plastic material and are characterized by a predetermined opacity.

BACKGROUND OF THE INVENTION

The natural tooth has a colour gradient, differences in translucence and different lightnesses within the tooth. In order to reproduce the appearance of a natural tooth as realistically as possible, dental restorations are therefore usually also polychromatic and have a zonal structure with different areas which have colours that correspond to the natural tooth.

Particularly high demands are made on prostheses for the anterior tooth region. Here, artificial teeth with at least two and usually three to four layers are used as standard in order to achieve natural-looking aesthetics. These layers are composed of a transparent incisal material, an opaque dentine material and an even more opaque cervical material, wherein the dentine layer is primarily responsible for the colour effect.

Especially in the case of artificial prefabricated prosthetic teeth, a large amount of effort is therefore required in order to achieve an aesthetic effect that is acceptable in terms of colour with different tooth sizes and tooth shapes. In the posterior tooth region, although aesthetics play a less important role than in the case of anterior teeth, they are becoming increasingly important.

As part of digitalization and the introduction of CAD/CAM processes, prosthetic teeth manufactured to be patient-specific have also increasingly been used for the production of removable prostheses. When teeth and in particular tooth segments formed by several teeth stuck together are milled from multilayer blanks, it is difficult to achieve an aesthetically satisfactory appearance over the whole restoration, because the restoration generally cannot be positioned such that all areas of the restoration lie in the layer of the blank that is optimal for them. Moreover, the blank cannot be utilized optimally, which is associated with a relatively large quantity of waste. The production of more than one restoration from one blank is therefore not feasible. Even when multilayer blanks are used, it is usual to veneer the restorations after the milling.

DE 198 23 530 A1 discloses cuboid-shaped and cylindrical blocks made of dental resin materials which are to be suitable for the production of dental prostheses such as crowns or inlays by milling processing. The dental resin material contains acrylic resin polymer and 20 to 70 wt.-% inorganic filler with an average particle size of from 0.01 to 0.04 µm. Cylindrical blocks have a diameter of 15 mm and a height of 25 mm, for example. In order to adapt the colour to the surrounding teeth, the restorations can also be veneered.

Blanks for the production of dental prostheses, which contain a polymer resin and a finely dispersed filler material with a maximum particle diameter of 50 µm, are known from WO 00/40206. The blanks are characterized in that they are free from cracks and are produced such that they pass a thermal shock test. The appearance of the prostheses can be adapted by the application of additional materials.

SUMMARY OF THE INVENTION

The object of the invention is to provide dental shaped bodies and blanks for the production of dental restorations which have an appearance that matches a natural tooth and which are easy to produce and to process. The object of the invention is in particular to provide artificial teeth and tooth segments that satisfy high aesthetic demands and blanks which are suitable for the production of artificial teeth and tooth segments by milling processing.

BRIEF DESCRIPTION OF THE DRAWINGS

Further advantages, details and features will arise from the following illustration of the invention using several examplary embodiments, while reference is made to the drawing, wherein.

DETAILED DESCRIPTION

An object of the invention is achieved by monochromatic dental shaped bodies which have an opacity of from 70 to 78%. The shaped bodies are preferably in the form of a dental restoration or in the form of a blank for the production of a dental restoration. The dental restoration is preferably an artificial tooth or a tooth segment. By a tooth segment is meant a shaped body which is formed by two or more, preferably 2 to 14 and in particular 2 to 7 artificial teeth joined to each other. The blank is particularly suitable for further processing by cutting processes, such as milling processing or CAD/CAM processes.

It was surprisingly found that a monochromatic material in a tightly restricted opacity range makes it possible to produce aesthetically appealing, natural-looking dental restorations. This effect is to be attributed to a kind of chameleon effect which is based on an interaction of opacity and outer shape of the shaped bodies. In the case of tooth-shaped shaped bodies, the outer contour of the tooth and the associated variation in the material thickness within the found opacity range lead to a natural-looking appearance. The colour effect is more pronounced and the material looks more opaque where the tooth is thicker and therefore the layer thickness is greater. Conversely, the colour effect is less pronounced and the material looks more transparent and lighter where the tooth and therefore the layers are thinner. On the whole, a very natural-looking colour and translucence gradient is thus achieved by a simple measure.

Shaped bodies with an opacity of from 72 to 76%, particularly preferably 73 to 75% and quite particularly preferably approx. 74% are preferred according to the invention. The opacity O is the ratio of the incident luminous flux $I_0$ to the transmitted luminous flux I: $O=I_0/I$. The inverse of opacity is transmittance. According to the invention the opacity of test pieces with a diameter of 20 mm and a height of 2±0.02 mm is measured. The measurement can be effected with measuring instruments customary in the trade, preferably with a Minolta CM-3700d spectrophotometer (wavelength 360 to 740 nm).

The effect occurs in principle in all materials which have an opacity within the range according to the invention after the colouring to a tooth-coloured shade. The shaped bodies can therefore consist, for example, of dental ceramic or plastic.

Shaped bodies made of plastics which are obtained by polymerization of organic monomers are preferred according to the invention. The plastics can be filled or unfilled. By filled plastics is meant plastics which, in addition to the polymerized resin matrix, contain at least one filler homogeneously dispersed therein. The shaped bodies are obtained by homogeneously dispersing one or more fillers in a polymerizable resin. The mixture is then brought into the desired shape and cured by polymerization. The curing is preferably effected by the introduction of energy in the form of temperature, pressure or electromagnetic radiation, but the use of cold-curing initiator systems is in principle also possible. The curing is preferably effected thermally.

Cationically and in particular radically polymerizable monomers are preferred as polymerizable resins. One or more monofunctional monomers or a mixture of monofunctional and polyfunctional monomers are particularly preferably used as resin. By monofunctional monomers is meant compounds with one, by polyfunctional monomers is meant compounds with two or more, preferably 2 to 4 and in particular 2 cationically or radically polymerizable groups.

For example, N-monosubstituted acrylamides such as e.g. N-ethylacrylamide can be used as monofunctional radically polymerizable monomers. Monofunctional radically polymerizable monomers preferred according to the invention are mono(meth)acrylates. Particularly preferred monofunctional (meth)acrylates are methyl (meth)acrylate, ethyl (meth)acrylate, 2-hydroxyethyl (meth)acrylate, butyl (meth) acrylate, isobutyl (meth)acrylate, acetoxyacetylethyl (AAE) (meth)acrylate, benzyl (meth)acrylate, tetrahydrofurfuryl (meth)acrylate, isobornyl (meth)acrylate and p-cumyl-phenoxyethylene glycol (meth)acrylate (CMP-1E) and mixtures thereof; isobutyl (meth)acrylate, tetrahydrofurfuryl (meth) acrylate or isobornyl (meth)acrylate, CMP-1E and mixtures thereof are quite particularly preferred. Methyl methacrylate (MMA) is most preferred.

For example, N-disubstituted acrylamides, such as e.g. N,N-dimethylacrylamide, and bisacrylamides, such as e.g. N,N'-diethyl-1,3-bis(acrylamido)-propane, 1,3-bis(methacrylamido)-propane, 1,4-bis(acrylamido)-butane or 1,4-bis(acryloyl)piperazine, can be used as polyfunctional radically polymerizable monomers. According to the invention polyfunctional and in particular difunctional (meth)acrylates are preferred, such as e.g. di-, tri- or tetraethylene glycol di(meth)acrylate, trimethylolpropane tri(meth)acrylate, pentaerythritol tetra(meth)acrylate, as well as glycerol di- and tri(meth)acrylate, 1,4-butanediol di(meth)acrylate, 1,12-dodecanediol di(meth)acrylate and mixtures thereof.

Particularly preferred dimethacrylates are bisphenol A dimethacrylate, 2,2-bis[4-(2-hydroxy-3-methacryloyloxypropyl)-phenyl]propane (bis-GMA; an addition product of methacrylic acid and bisphenol A diglycidyl ether), ethoxy- or propoxylated bisphenol A dimethacrylate, such as e.g. the bisphenol A dimethacrylate 2-[4-(2-methacryloyloxy-ethoxyethoxy)phenyl]-2-[4-(2-methacryloyloxyethoxy)phenyl]propane (CAS No. 41637-38-1, SR-348c, Sartomer), 2-(((2-(N-methyl-acrylamido)ethoxy)carbonyl)amino)ethyl methacrylate and 2,2-bis[4-(2-methacryloxypropoxy)phenyl]propane, bis-(3-methacryl-oyloxymethyl)tricyclo-[5.2.1.0$^{2,6}$]decane (DCP) and mixtures thereof. Quite particularly preferred polyfunctional monomers are urethane dimethacrylates (UDMA, 1,6-bis-[2-methacryloyloxy-ethoxycarbonylamino]-2,2,4-trimethylhexane; TMX-UDMA (an addition product of a mixture of HEMA and hydroxypropyl methacrylate (HPMA) with α, α, α', α'-tetramethyl-m-xylylene diisocyanate (TMXDI)), 1,10-decanediol dimethacrylate (D$_3$MA), ethylene glycol dimethacrylate and mixtures thereof.

A monomer mixture that is particularly advantageous according to the invention is a mixture of the monomers MMA, UDMA (or TMX-UDMA) and ethylene glycol dimethacrylate, wherein the monomers are preferably used in a weight ratio of from 9 to 12 parts by weight MMA, 0.5 to 2 parts by weight UDMA (or TMX-UDMA) and 1 part by weight ethylene glycol dimethacrylate.

In the case of unfilled materials, plastics based on or made of polymethyl methacrylate (PMMA) are preferred.

According to the invention, however, plastics which contain at least one filler are preferred. The filler(s) can be of an inorganic, organic-inorganic or preferably organic nature, wherein particulate fillers are preferred.

Preferred inorganic particulate fillers are powders of radiopaque glasses with an average particle size of from 0.01 to 15 µm, preferably 0.10 to 5.0 µm; radiopaque fillers, such as ytterbium trifluoride, with an average particle size of from 0.050 to 2.0 µm, preferably 0.10 to 1.0 µm; SiO$_2$, ZrO$_2$, ZnO as well as mixed oxides made of SiO$_2$, ZrO$_2$, ZnO and/or TiO$_2$ with an average particle size of from 5 to 500 nm, preferably 20 to 200 nm; nanoparticulate fillers, such as tantalum(V) oxide, barium sulphate or mixed oxides of SiO$_2$ with ytterbium(III) oxide or tantalum(V) oxide with an average particle size of from 5 to 500 nm, preferably 20 to 200 nm. ZrO$_2$ and BaSO$_4$ are particularly suitable for adjusting the opacity.

Polymer particles, in particular particles of crosslinked organic polymers, are preferred as organic fillers. Polymer particles can be obtained by curing one or more monomers and then grinding the cured mixture or by suspension polymerization. The curing can be effected by light or thermally. Radically polymerizable monomers and in particular the monomers listed above are preferred as monomers. Dimethacrylates, specifically bis-GMA, UDMA, TMX-UDMA, DCP, D$_3$MA and mixtures thereof, are quite particularly preferred.

Polymer particles which are prepared by grinding exhibit a splintery appearance under the microscope and are therefore also referred to as splinter polymerisates or splinter polymers. The pearl polymerisates obtained by suspension polymerization in contrast are characterized by spherical particles. Splinter polymerisates are preferred as organic fillers.

By organic-inorganic fillers is meant polymer particles which are themselves filled with inorganic fillers. Such fillers are also referred to as composite fillers. Organic-inorganic fillers are preferably prepared by curing mixtures based on radically polymerizable monomers and inorganic fillers. The curing can be effected light-induced or preferably thermally. Preferably dimethacrylates and particularly preferably bis-GMA, UDMA, TMX-UDMA, DCP and/or D$_3$MA are used as radically polymerizable monomers. Fumed or precipitated silicas, radiopaque glass fillers, ytterbium trifluoride and mixtures of these components are preferably used as fillers. The refractive index of the polymerized monomer mixture is preferably set such that it largely corresponds to the refractive index of the main filler used. In this manner it is achieved that the composite filler has a high transparency. The polymerisates are ground and used as a powder.

The organic or organic-inorganic fillers preferably have an average particle size of from 2 to 100 µm, particularly preferably 2 to 60 µm or 5 to 60 µm, quite particularly preferably of from 10 to 50 µm, most preferably of from 10 to 30 µm and in particular approx. 20 µm. All particle sizes of splinter or pearl polymers are averaged d50 values, which can be measured e.g. in a particle size measuring instrument of the Horiba LA-960 Laser Particle Size Analyzer type (HORIBA Ltd. Kyoto/Japan). The measurement is effected by means of laser diffraction spectroscopy. The samples to be analyzed are dispersed in a suitable auxiliary agent such as e.g. a 20% aqueous solution of sodium polyphosphate (inorganic samples) or an aqueous 0.5 wt.-% Tween solution (polyoxyethylene sorbitan monolaurate solution). The results are calculated according to the rules of the Mie theory.

In order to achieve an as natural as possible appearance of dental restorations, the plastics according to the invention preferably contain at least one composite filler and particularly preferably at least one organic filler which has a higher transparency, i.e. a lower opacity, than the matrix material. The above-described crosslinked polymer particles are particularly preferred. These fillers have a relatively large particle size and are able to guide light deep into the inside of the material, with the result that a particular depth effect occurs, which gives the restoration a natural visual appearance.

The filled or unfilled plastics preferably contain at least one colorant, wherein pigments are preferred as colorant. Materials which contain one or more pigments, which are selected from the following substances, are particularly preferred:

| Name | Type | Chem. name | CAS No. |
|---|---|---|---|
| Microlith* yellow | Yellow 1550K* | 2,2'-[(3,3'-dichloro[1,1'-biphenyl]-4,4'-diyl)bis(2,1-diazenediyl)]bis[N-(4-chloro-2,5-dimethoxyphenyl)-3-oxo-butanamide | 5567-15-7 |
| | Yellow 1040K* | 3,3'-[(2-chloro-5-methyl-1,4-phenylene)bis[imino(1-acetyl-2-oxo-2,1-ethanediyl)-2,1-diazenediyl]]bis[4-chloro-N-(3-chloro-2-methylphenyl)-benzamide | 5580-57-4 |
| | Yellow 2040K* | 3,3'-(1,4-phenylenedinitrilo)bis[4,5,6,7-tetrachloro-2,3-dihydro-1H-isoindol-1-one | 5590-18-1 |
| | Yellow 1061K* | 2-[2-[1-[[(2,3-dihydro-2-oxo-1H-benzimidazol-5-yl)amino]carbonyl]-2-oxopropyl]diazenyl]-benzoic acid | 31837-42-0 |
| Microlith* red | Red 3890K* | N,N'-(2-chloro-1,4-phenylene)bis[4-[2-(2,5-dichlorophenyl)diazenyl]-3-hydroxy-2-naphthalenecarboxamide | 5280-78-4 |
| | Red 3430K* | 1,4-bis[1-[(2,5-dichlorophenyl)azo]-2-hydroxynaphthalen-3-ylcarbonylamino]benzene | 3905-19-9 |
| | Red 4410K* | N-(2,3-dihydro-2-oxo-1H-benzimidazol-5-yl)-3-hydroxy-4-[2-[2-methoxy-5-methyl-4-[(methylamino)sulphonyl]phenyl]diazenyl]-2-naphthalenecarboxamide | 51920-12-8 |
| | Red 3630K* | 3,6-bis(4-chlorophenyl)-2,5-dihydropyrrolo[3,4-c]pyrrole-1,4-dione | 84632-65-5 |
| Kronos** | Kronos 1171** | titanium dioxide (anatase type) | 13463-67-7 |
| | Kronos 2971** | titanium dioxide (rutile type) | 13463-67-7 |
| Sicovit*** | Yellow 10 | iron hydroxide oxide (FeO(OH)) | 51274-00-1 |
| | Black 80 | iron oxide | 12227-89-3 |
| | Black 85 | iron oxide | 12227-89-3 |
| Lumilux**** | LZ Blue | Terephthalic acid ester | 658084-50-5 |
| | Blue CD 312 | pyrazoline derivative | 192464-72-5 |

*Microlith is a registered trade mark of BASF SE, GVX/W-C6 Carl-Bosch-Strasse 38, 67056 Ludwigshafen am Rhein, (DE)
**Kronos is a registered trade mark of KRONOS TITAN GmbH Peschstrasse 5, 51373 Leverkusen, (DE) (Kronos International Inc.)
***Sicovit is a registered trade mark of Rockwood Italia S.p.A., Via G. Reiss Romoli, 44/12 I-10148 Turin, (IT) (formerly BASF SE)
****Lumilux is a registered trade mark of Honeywell Specialty Chemicals Seelze GmbH, Wunstorfer Strasse 40, 30926 Seelze, (DE)

Particularly preferred pigments are iron oxide black, iron hydroxide oxide yellow, $TiO_2$ white, Microlith red, Microlith yellow and mixtures thereof.

The colorants are preferably adjusted such that the materials are tooth-coloured after the curing. The shaped bodies particularly preferably have one of the following colours after the curing:

| Colour | L*a*b* values | | |
|---|---|---|---|
| | L | a | b |
| BL3 | 86.0 | 3.4 | 15.5 |
| A1 | 84.0 | 5.0 | 22.3 |
| A2 | 79.5 | 7.7 | 26.4 |
| A3 | 78.5 | 8.3 | 29.0 |
| A3.5 | 76.5 | 9.5 | 31.4 |
| B1 | 82.5 | 3.8 | 21.4 |
| B3 | 78.0 | 7.4 | 32.0 |
| C2 | 75.5 | 6.3 | 25.4 |
| D2 | 77.5 | 5.9 | 22.3 |

The colours are determined according to the L*a*b* colour model corresponding to DIN EN ISO 11664-4. The colour measurement can be carried out with measuring instruments customary in the trade such as the Minolta CM-3700d colour-measuring instrument.

The colour designations A1, A2, A3 etc. correspond to the Vita colour system (Vita Lumin-VACUUM shade guide). This is a colour scale that is common and widely used in the dental field. These designations allow a person skilled in the art to quickly correlate the colours.

The materials according to the invention preferably contain 0.0002 to 1.0 wt.-%, particularly preferably 0.001 to 0.25 wt.-% pigment(s), relative to the total mass of the material.

The plastics furthermore preferably contain a thickener. Uncrosslinked polymer particles are preferred as thickener, in particular pearl polymers which can advantageously be prepared by suspension polymerization. Radically polymerizable monomers and in particular the monomers listed above are preferred as monomers. Mono(meth)acrylates, in particular methyl methacrylate (MMA), are quite particularly preferred. In the initial state, the uncrosslinked polymer particles preferably have an average particle size of from 10 to 120 µm, particularly preferably 10 to 60 µm and quite particularly preferably approx. 50 µm. The uncrosslinked polymer particles differ from the crosslinked polymer particles used as filler in that they are at least partially soluble in the monomers used as matrix material and can thus alter their particle size. They are therefore not regarded as fillers.

In order to produce shaped bodies, the named components and optionally further additives are mixed homogeneously with each other, the mixture is brought into the desired shape and then cured by polymerization.

In particular initiators for the radical and/or cationic polymerization, stabilizers, such as e.g. polymerization stabilizers, antibacterial agents, fluoride ion-releasing additives, optical brighteners, fluorescent agents, UV absorbers, antifoams, thixotropic adjuvants, substances for improving the fracture toughness and/or effect agents come into consideration as further additives.

Thermal as well as radiation-activated initiators known to a person skilled in the art come into consideration as initiators for the described systems. Conventional thermal initiators are lauroyl peroxide, tert-butyl peroxide, cumene hydroperoxide or also azoisobutyronitrile. Benzoyl peroxide is particularly preferred, which can also be encapsulated in the PMMA pearl polymers, as is customary in dental plastics. Combinations with tertiary, usually aromatic amines such as N,N-dimethyl-p-toluidine or N,N-diethanol-p-toluidine (DEPT) as accelerators can be used as initiator systems initiating at room temperature. Known photosensitizers are diketones such as e.g. 9,10-phenanthrenequinone, 1-phenyl-propane-1,2-dione, diacetyl or 4,4'-dichlorobenzil or derivatives thereof; camphorquinone (CQ) and derivatives thereof are particularly preferred, and mixtures thereof.

The listed photoinitiators are preferably used in combination with accelerators. Tertiary amines such as e.g. tertiary aromatic amines, in particular N,N-dialkyl-anilines, -p-toluidines or -3,5-xylidines, p-(N,N-dialkylamino-phenylethanol, -benzoic acid derivatives, -benzaldehyde, -phenylacetic acid ester and -phenylpropionic acid ester are particularly suitable as accelerators for photoactive systems. Specific examples thereof are N,N-dimethylaniline, N,N-dimethyl-p-toluidine, N,N,3,5-tetramethylaniline, N,N-dimethyl-amino-p-benzaldehyde, p-(dimethylamino)-benzoic acid ethyl ester or p-(dimethylamino)-benzonitrile. Tertiary aliphatic amines, such as e.g. tri-n-butylamine, dimethylaminoethan-2-ol, triethanolamine, dimethylaminoethyl methacrylate, N,N-dimethylbenzylamine, or heterocyclic amines, such as e.g. 1,2,2,6,6-pentamethylpiperidine, and amino acid derivatives, such as e.g. N-phenylglycine, are also suitable. Particularly preferred photoinitiators are acyl- or bisacylgermanium compounds, in particular the monoacyltrialkyl- and bisacyldialkylgermanium compounds disclosed in EP 1 905 413 A1, such as e.g. benzoyltrimethylgermanium, bisbenzoyldiethylgermanium or bis(4-methoxybenzoyl)diethylgermanium. Acyl- and bisacylgermanium compounds have the advantage that they are discoloured after irradiation (bleaching effect), and therefore in the case of prolonged use of the shaped bodies produced by means of these no colour changes occur. In addition, they are monomolecular photoinitiators, i.e. they do not require an accelerator in order to reach their full activity. Further particularly preferred photoinitiators are acyl- or bisacylphosphine oxides, in particular the compounds described in EP 0 007 505, EP 0 073 413, EP 0 184 095 and EP 0 615 980. Preferred examples are the commercially available compounds 2,4,6-trimethylbenzoyl-diphenylphosphine oxide (Lucirin® TPO, BASF) and bis(2,4,6-trimethylbenzoyl)phenylphosphine oxide (Irgacure® 819, Ciba). Acyl- and bisacylphosphine oxides also belong to the group of the monomolecular photoinitiators and are characterized by a low self-absorption.

In order to adjust the desired opacity, the procedure is preferably such that resin and optionally filler are mixed and coloured by the addition of the colorant(s), then the opacity is measured and subsequently adjusted.

The pigment titanium dioxide has a refractive index $n_D^{20}$ of 2.52, which is much higher than that of most matrix materials, and thus already allows an extensive adjustment of the opacity during the coloration.

Should the opacity still lie below the above-defined values after the coloration, it can be increased by the addition of further pigments, in particular $TiO_2$, and/or of a filler the refractive index of which deviates from that of the matrix material. The adjustment is preferably effected using fine-particle inorganic fillers such as $SiO_2$, $ZrO_2$ and/or $BaSO_4$ with a particle size of from 5 to 500 nm, preferably 20 to 200 nm. Should the measured opacity be too high, it can be reduced by addition of matrix material or of a filler with a matrix-like refractive index.

According to an embodiment of the invention, shaped bodies are preferred which do not contain an inorganic filler and particularly preferably do not contain a composite filler either. In this case, the opacity is adjusted by the addition of one or more pigments, preferably by the addition of $TiO_2$.

The mixture can be shaped to form shaped bodies in different ways. According to an embodiment, the mixture is poured into a suitable casting mould and then cured. In this way, e.g., cuboid-shaped, cube-shaped or cylindrical blanks or blanks with another three-dimensional shape such as prosthetic teeth and tooth segments can be produced. In this embodiment, the mixtures are preferably cured thermally.

According to an alternative embodiment, the mixture is shaped to form shaped bodies by additive processes and preferably cured in layers. A preferred additive process is stereolithography. In additive processes the curing is preferably effected by light.

Mixtures which are particularly suitable for casting processes preferably have the following composition:
(1) 1 to 20 wt.-%, preferably 2 to 15 wt.-% and quite particularly preferably 3 to 12 wt.-% polyfunctional radically polymerizable monomer(s),
(2) 10 to 60 wt.-%, preferably 5 to 50 wt.-% and quite particularly preferably 10 to 45 wt.-% monofunctional radically polymerizable monomer(s),
(3) 0.01 to 5.0 wt.-%, preferably 0.1 to 3.0 wt.-% and quite particularly preferably 0.1 to 2.0 wt.-% initiator for the radical polymerization,
(4) 5 to 90 wt.-%, preferably 10 to 85 wt.-% and quite particularly preferably 20 to 80 wt.-% filler(s), and optionally
(5) 0.1 to 5.0 wt.-%, preferably 0.1 to 2.0 wt.-% and quite particularly preferably 0.2 to 1.5 wt.-% further additive(s), in each case relative to the total mass of the mixture.

Mixtures which have the following composition are preferred:
(1) 1 to 20 wt.-%, preferably 2 to 15 wt.-% and quite particularly preferably 3 to 12 wt.-% polyfunctional radically polymerizable monomer(s),
(2) 10 to 60 wt.-%, preferably 5 to 50 wt.-% and quite particularly preferably 10 to 45 wt.-% monofunctional radically polymerizable monomer(s),
(3) 0.01 to 5.0 wt.-%, preferably 0.1 to 3.0 wt.-% and quite particularly preferably 0.1 to 2.0 wt.-% initiator for the radical polymerization,
(4) 20 to 90 wt.-%, preferably 35 to 80 wt.-% and quite particularly preferably 45 to 70 wt.-% thickener, preferably uncrosslinked polymer particles, and optionally
(5) 0.1 to 5.0 wt.-%, preferably 0.1 to 2.0 wt.-% and quite particularly preferably 0.2 to 1.5 wt.-% further additive(s), in each case relative to the total mass of the mixture.

Mixtures which have the following composition are particularly preferred:
(1) 1 to 20 wt.-%, preferably 2 to 10 wt.-% and quite particularly preferably 3 to 8 wt.-% polyfunctional radically polymerizable monomer(s),
(2) 10 to 60 wt.-%, preferably 5 to 50 wt.-% and quite particularly preferably 10 to 45 wt.-% monofunctional radically polymerizable monomer(s),
(3) 0.01 to 5.0 wt.-%, preferably 0.1 to 3.0 wt.-% and quite particularly preferably 0.1 to 2.0 wt.-% initiator for the radical polymerization,
(4) 20 to 70 wt.-%, preferably 30 to 60 wt.-% and quite particularly preferably 35 to 55 wt.-% thickener, preferably uncrosslinked polymer particles, (5) 5 to 50 wt.-%, preferably 10 to 40 wt.-% and quite particularly preferably 15 to 35 wt.-% organic filler, preferably crosslinked polymer particles, and optionally
(6) 0.1 to 5.0 wt.-%, preferably 0.1 to 2.0 wt.-% and quite particularly preferably 0.2 to 1.5 wt.-% further additive(s), in each case relative to the total mass of the mixture.

Preferred mixtures which are particularly suitable for additive processes preferably have the following composition:
(1) 15 to 70 wt.-%, preferably 20 to 60 wt.-% and quite particularly preferably 25 to 50 wt.-% mono- and/or polyfunctional radically polymerizable monomer(s),
(2) 0.01 to 5.0 wt.-%, preferably 0.1 to 3.0 wt.-% and quite particularly preferably 0.1 to 2.0 wt.-% photoinitiator for the radical, cationic or combined polymerization,
(3) 5 to 90 wt.-%, preferably 10 to 85 wt.-% and quite particularly preferably 30 40 to 80 wt.-% filler(s), and optionally
(4) 0.1 to 5.0 wt.-%, preferably 0.1 to 2.0 wt.-% and quite particularly preferably 0.2 to 1.5 wt.-% further additive(s), in each case relative to the total mass of the mixture.

In all cases, the above-defined mixtures preferably contain in each case 0.0002 to 1.0 wt.-%, particularly preferably 0.001 to 0.25 wt.-% pigment(s), relative to the total mass of the mixture.

The use of the uncured mixtures for the production of shaped bodies by constructive or additive processes is likewise a subject of the invention.

Another subject of the invention is a process for the production of shaped bodies in which:
(a) a polymerizable mixture is provided by mixing polymerizable matrix, optionally filler and optionally additives,
(b) the mixture is coloured by the addition of colorants,
(c) if necessary the opacity of the mixture is optionally adjusted by the addition of fine-grained filler, preferably $ZrO_2$ and/or $BaSO_4$, and/or pigment(s),
(d) the mixture is shaped to form a shaped body and
(e) cured by radical and/or cationic polymerization.

The shaped body is preferably subjected, after the curing, to a subsequent age hardening (step f), e.g. by tempering at elevated temperatures, ideally in the temperature range of from 20 to 90° C., and/or irradiation with light, ideally with wavelengths of from 300 to 500 nm. Through the subsequent age hardening the extent of the polymerization is increased and the residual monomer content is reduced.

According to a preferred embodiment of the invention, the shaped body is shaped in step (d) by introducing the mixture into a casting mould, for example a steel mould, by injection moulding followed by curing in step (e). The curing is preferably effected thermally, e.g. in a hydraulic press for 20 minutes at a temperature of 140° C. and a pressure of 30 bar.

According to a further preferred embodiment of the invention, the mixture is shaped to form a shaped body in step (d) by an additive process, preferably by stereolithography. The shaped body can be cured by radical and/or cationic polymerization in its entirety after the finishing or in layers during the production. The curing in layers is preferably effected photochemically. Additive processes are particularly suitable for the production of shaped bodies which are in the form of teeth or tooth segments.

Additive manufacturing processes are also referred to as constructive, depositing or additive processes. The terms "additive manufacturing" or "3D printing" are also usual.

The shaped bodies are preferably in the form of teeth, tooth segments, blocks or discs. Shaped bodies for use as blanks are preferably in the form of cylindrical blocks with a diameter of from 80 to 110 mm, preferably 90 to 100 mm, in particular approx. 100 mm and a thickness of from 10 to 30 mm. These cylindrical blocks are particularly suitable as blanks for the manufacture of dental restorations such as teeth or tooth segments by cutting processes. For this the blank is shaped to form a dental shaped part, for example in a dental laboratory or a dental clinic. This can preferably be effected by milling or grinding by means of a CAD/CAM system. The teeth and tooth segments milled from these discs are characterized by excellent aesthetics and can be used without further processing, i.e. in particular without veneering, for the production of prostheses.

The invention also relates to the use of the blanks or shaped bodies according to the invention for the production of dental restorations. The dental restoration here is preferably a tooth or a tooth segment or a partial or full prosthesis which was produced using these teeth or tooth segments.

The materials according to the invention are advantageous in many respects. The shaped bodies according to the invention do not have a layer structure but instead have a homogeneous composition, which simplifies the production of blanks and artificial teeth. Moreover, bonding problems between the layers are avoided. The shaped bodies are characterized by a high material homogeneity, with the result that stresses in the material are prevented. In the case of blanks, the restorations to be milled can be freely positioned without layer-induced restrictions, which facilitates an optimal utilization of the blanks, for example the milling of several restorations from one blank, and avoids unnecessary waste. Maximum milling freedom is provided, which makes the production of large blanks economical. In the case of the production of tooth segments, the monochromacity is advantageous because connectors between the teeth joined to each other are less conspicuous.

In the case of constructive/additive manufacturing processes the whole process can be carried out with one material. It is not necessary to change the material during the construction process, and the provision of data can be substantially simplified because only one envelope is required for the whole component.

The advantages sought according to the invention become particularly clear when the shaped body has a tooth geometry, i.e. at the same time areas with a large and a small layer thickness. The production of shaped bodies with a small layer thickness such as crowns and veneers (shells) is possible, but requires the tooth stumps in the patient's mouth to be covered with a colour-matched opaquer layer.

The teeth and tooth segments manufactured from the materials according to the invention are suitable in particular for the production of anterior teeth for removable full and partial prostheses. The teeth in addition exhibit a high degree of conformity with the shade guides used as standard in the dental field and are compatible with commercially available artificial teeth, which is advantageous with regard to the repair of existing prostheses.

The invention is described in more detail below by means of figures and embodiment examples.

Figure 1:
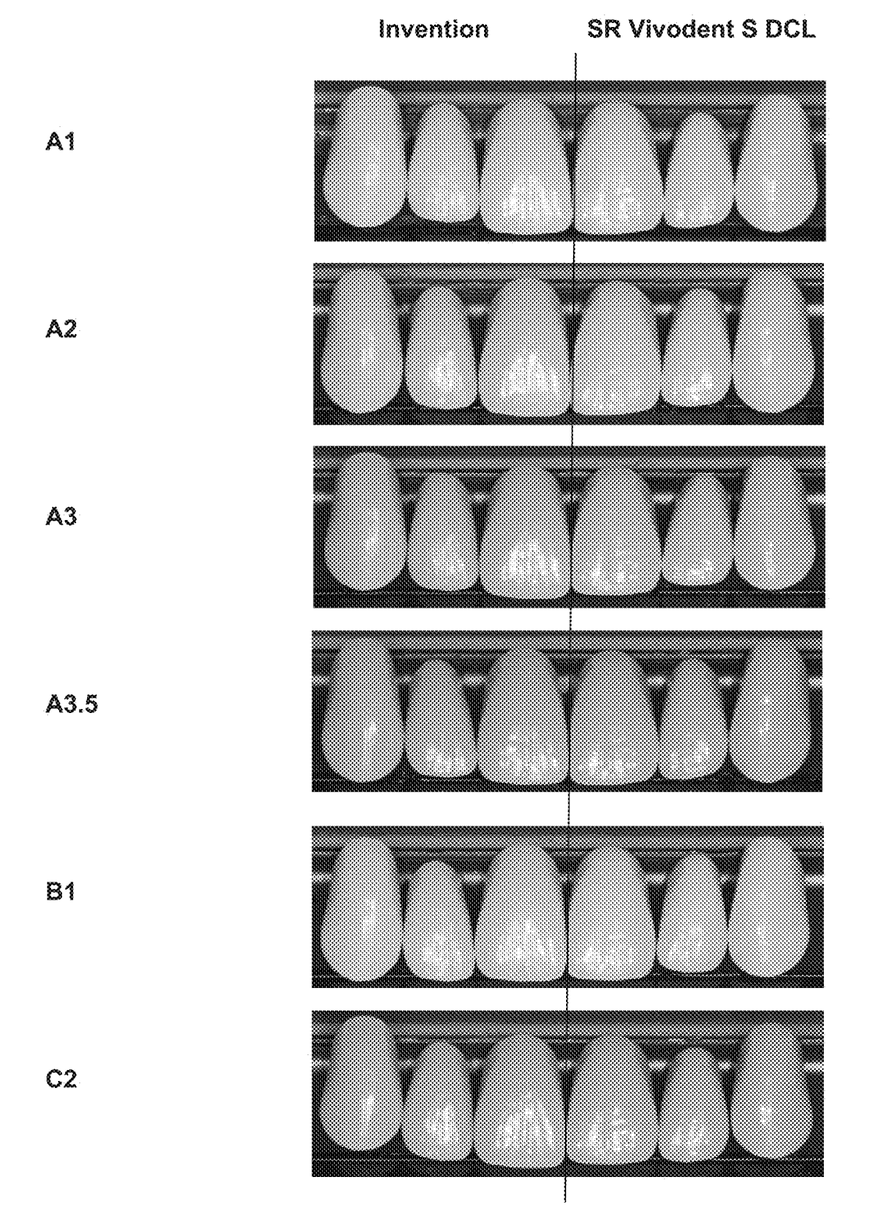
FIG. 1 shows teeth milled from blanks according to the invention in comparison with plastic teeth customary in the trade of the same colour with a multilayer structure.

FIG. 1 shows teeth milled from blanks according to the invention in comparison with plastic teeth customary in the trade of the same colour with a multilayer structure.

EMBODIMENT EXAMPLES

Example 1

Preparation of a Polymerizable Composition for the Production of Shaped Bodies

The components indicated in Table 1 were mixed with each other to form a homogeneous mixture. In order to achieve a as homogeneous as possible pigment distribution, the pigments were firstly mixed homogeneously with the uncrosslinked polymer particles (see Table 2) and this mixture was then mixed with the remaining components. Test pieces with a diameter of 20 mm and a height of 2±0.02 mm were polymerized from the mixture formed. The polymerization was effected in a pressure polymerizer (Ivomat IP3, Ivoclar Vivadent AG) at 120° C. under water at a pressure of 6 bar for 15 min. The obtained test pieces were wet-polished with a wet-grinding machine with sandpaper (P4000 grit) before the colour and opacity measurement. The opacity and colour measurements were effected with a Minolta CM-3700d colour-measuring instrument. This instrument uses a xenon flash (pulsed xenon arc lamp, wavelength 360 to 740 nm). The colour was measured corresponding to the L*a*b* colour model according to DIN EN ISO 11664-4. The results are shown in Table 3.

TABLE 1

Compositions for the production of shaped bodies

| | Component | Ex. 1a | Ex. 1b |
|---|---|---|---|
| Monomer | methyl methacrylate (MMA) CAS 80-62-6 | 80 g | 80 g |
| | urethane dimethacrylate(UDMA) CAS 72869-86-4 | 12.5 g | — |
| | TMX-UDMA CAS 1809948-82-0 | — | 10 g |
| | ethylene glycol dimethacrylate CAS 97-90-5 | 7.5 g | 10 g |
| Thickener | PMMA powder (average grain size 40 to 60 μm)* CAS (PMMA) 9011-14-7 | 119 g | 139 g |
| Filler | polymer powder (UDMA polymerized and ground to an average grain size of 20 μm) | 80 g | — |
| | polymer powder (TMX-UDMA polymerized and ground to an average grain size of 15 μm) | — | 60 g |
| Initiator | benzoyl peroxide CAS 94-36-0 | 1 g | 1 g |

*Mixture of uncrosslinked pearl polymer particles and pigments according to Table 2

TABLE 2

Composition of the mixture of PMMA powder and pigments

| Components | Weight-% |
|---|---|
| PMMA pearl polymer | 99.8606 |
| $TiO_2$ white pigment | 0.1200 |
| Microlith Yellow types | 0.0089 |
| Sicovit Yellow | 0.0032 |
| Sicovit Black | 0.0022 |
| Microlith Red | 0.0029 |
| Lumilux fluorescent agent | 0.0022 |
| Total | 100.0000 |

TABLE 3

Colour and opacity of Ex. 1a/b after 1st coloration

L*a*b* values according to L*a*b* colour system

| Colour*) A3 | L Lightness | A red-green | B yellow-blue | Opacity |
|---|---|---|---|---|
| Ex. 1a | 77.51 | 9.03 | 29.71 | 73.95 |
| Ex. 1b | 77.40 | 8.72 | 30.16 | 73.90 |

*)Colour designation according to Vita Lumin-VACUUM shade guide

In Example 1, the desired opacity was achieved by the combination of PMMA powder (thickener) and organic filler (crosslinked polymer; splinter polymer). The shaped bodies are characterized by a natural translucence, light scattering and colour effect.

Example 2

Production of Tooth-Shaped Shaped Bodies

For production of tooth-shaped shaped bodies firstly cylindrical blanks with appropriate dimensions were produced and then prosthetic teeth were milled therefrom. The blanks were produced from materials based on the formulation from Example 1, which were coloured according to requirements. After adjustment of the base colour, the opacity was measured as described in Example 1 using test pieces. The remaining powder mixture was then adjusted to the opacity values named in Table 4 by the addition of further $TiO_2$. The material was polymerized to form discs after the coloured powder mixtures with monomer had been made into a paste (mixing ratio see Table 1), in each case in a steel mould by means of a hydraulic hot press at 140° C. and a pressure of 30 bar for 20 min. Teeth with the external geometry of existing ready-made prosthetic teeth were milled from the thus-produced discs using a dental milling machine (Zenotec Select Ion, Wieland Dental). The teeth had a very natural appearance (FIG. 1) and can be used directly for the production of prostheses without veneering.

TABLE 4

Colour and opacity of tooth-shaped shaped bodies

L*a*b* values according to L*a*b* colour system

| Colour*) | L | a | b | Opacity |
|---|---|---|---|---|
| BL3 | 86.07 | 3.42 | 15.50 | 73.50 |
| A1 | 83.80 | 5.02 | 22.33 | 72.69 |
| A2 | 79.60 | 7.65 | 26.44 | 73.59 |
| A3 | 78.44 | 8.33 | 29.04 | 72.99 |
| A3.5 | 76.65 | 9.53 | 31.40 | 73.56 |
| B1 | 82.51 | 3.83 | 21.43 | 73.88 |
| B3 | 78.03 | 7.41 | 32.00 | 73.41 |
| C2 | 75.62 | 6.26 | 25.43 | 75.55 |
| D2 | 77.79 | 5.89 | 22.31 | 74.04 |

*)Colour designation according to Vita Lumin-VACUUM shade guide

Example 3

Comparison Example

Measurement of Conventional CAD Discs

The colour and the opacity of PMMA discs customary in the trade (PMMA-Telio CAD disc, Wieland Dental) were measured in the manner described in Example 1. The test pieces with a diameter of 20 mm and a height of 2±0.02 mm required for the measurement were milled from the blanks. The measured values are indicated in Table 5. In all colour shades the discs have a much higher opacity than blanks according to the invention. The discs are provided for the production of crowns. The opacity is high enough that the tooth stump is sufficiently covered, does not show through and does not have an adverse effect on the colour. According to Table 5, up to 81.49% of the incident luminous flux is blocked and a maximum of 21.47% of the incident light passes through the material. In the case of an opacity of 100%, the incident light would be completely blocked (0% passage); in the case of an opacity of 0%, 100% of the incident light would pass through the sample.

Artificial teeth which are produced from these discs differ from teeth made of materials according to the invention through a dull colour effect, which is reminiscent of the appearance of bone.

TABLE 5

Colour and opacity of customary PMMA discs[1]

L*a*b* values according to L*a*b* colour system

| Colour[2] | L | a | b | Opacity |
|---|---|---|---|---|
| BL3 | 86.29 | 2.24 | 15.07 | 81.49 |
| A1 | 84.17 | 3.96 | 21.01 | 78.80 |
| A2 | 81.64 | 6.44 | 25.25 | 78.53 |
| A3 | 77.17 | 8.61 | 25.27 | 79.87 |
| A3.5 | 75.37 | 11.29 | 29.69 | 78.96 |
| B1 | 85.13 | 1.48 | 20.53 | 79.78 |
| B3 | 75.09 | 9.40 | 29.17 | 80.56 |
| C2 | 72.82 | 6.36 | 22.96 | 79.79 |
| D2 | 75.22 | 6.50 | 20.16 | 79.13 |

[1](PMMA-Telio CAD for Zenotec, Wieland Dental)
[2]Colour designation according to Vita Lumin-VACUUM shade guide Example 4

Comparison Example

Measurement of Conventional Plastic Teeth

The colour and the opacity of the incisal layer and of the dentine layer of ready-made plastic teeth (Zahnlinie SR Vivodent S DCL, Ivoclar Vivadent AG) were measured in the manner described in Example 1. The test pieces with a diameter of 20 mm and a height of 2±0.02 mm required for the measurement were produced from the corresponding unpolymerized mixtures. The measured values are indicated in Tables 6 and 7. The measured values show that the dentine layer has a much higher opacity and the incisal layer a much lower opacity than the materials according to the invention. Nevertheless it was possible with the materials according to the invention from Example 4 to produce artificial teeth the appearance of which virtually matches the teeth customary in the trade. For 6 colour shades, in each case three teeth, which were milled from blanks according to the invention, are depicted in FIG. 1 together with in each case three teeth customary in the trade of the same colour. The match is astounding.

TABLE 6

Colour and opacity of the incisal layer of plastic teeth[1] customary in the trade

| Colour[2] | L*a*b* values according to L*a*b* colour system | | | Opacity |
|---|---|---|---|---|
| | L | a | b | |
| BL3 | 89.99 | 2.03 | 12.58 | 55.71 |
| A1 | 90.12 | 1.13 | 14.47 | 52.29 |
| A2 | 89.44 | 1.94 | 16.90 | 54.20 |
| A3 | 89.35 | 1.35 | 19.87 | 52.97 |
| A3.5 | 87.97 | 2.57 | 25.37 | 53.90 |
| B1 | 90.00 | 0.46 | 14.87 | 53.55 |
| B3 | 89.40 | 0.75 | 20.36 | 53.04 |
| C2 | 87.40 | 1.55 | 21.68 | 53.73 |
| D2 | 87.35 | 2.87 | 17.62 | 54.17 |

[1] Zahnlinie SR Vivodent S DCL, Ivoclar Vivadent AG
[2] Colour designation according to Vita Lumin-VACUUM shade guide

TABLE 7

Colour and opacity of the dentine layer of plastic teeth[1] customary in the trade

| Colour[2] | L*a*b* values according to L*a*b* colour system | | | Opacity |
|---|---|---|---|---|
| | L | a | b | |
| BL3 | 85.50 | 2.88 | 13.18 | 85.88 |
| A1 | 82.24 | 4.25 | 20.45 | 83.21 |
| A2 | 78.55 | 6.85 | 26.76 | 84.63 |
| A3 | 75.81 | 7.29 | 27.34 | 84.62 |
| A3.5 | 73.57 | 9.98 | 31.59 | 84.73 |
| B1 | 82.36 | 2.34 | 20.05 | 84.12 |
| B3 | 74.81 | 8.37 | 33.71 | 83.48 |
| C2 | 70.82 | 6.02 | 24.89 | 85.80 |
| D2 | 74.28 | 5.14 | 20.20 | 85.64 |

[1] Zahnlinie SR Vivodent S DCL, Ivoclar Vivadent AG
[2] Colour designation according to Vita Lumin-VACUUM shade guide

The invention claimed is:

1. Monochromatic dental shaped body comprising
a polymerized resin matrix,
a thickener comprising uncrosslinked polymer particles, and
at least one organic filler comprising crosslinked polymer particles having an average particle size (d50 value) of from 20 to 100 μm,
wherein the monochromatic dental shaped body has an opacity of from 72 to 76% and a color, determined according to the L*a*b color model corresponding to DIN EN ISO 11664-4, defined by an L value within the range of 75.5 to 86.0, an a value within the range of 3.4 to 9.5 and a b value within the range of 15.5 to 32.0, and wherein the monochromatic dental shaped body does neither contain inorganic filler nor organic-inorganic filler (composite filler) and does not have a layer structure.

2. Shaped body according to claim 1,
wherein the opacity is from 73 to 75%.

3. Shaped body according to claim 1,
wherein the polymeric resin matrix is formed by polymerization of a monomer or a mixture of monomers which is/are selected from monofunctional monomers, polyfunctional monomers or a mixture of mono- and polyfunctional monomers.

4. Shaped body according to claim 3,
wherein the monofunctional monomer(s) is/are selected from methyl methacrylate, ethyl methacrylate, 2-hydroxyethyl methacrylate, butyl methacrylate, benzyl methacrylate, tetrahydrofurfuryl methacrylate, isobornyl methacrylate, p-cumyl-phenoxyethylene glycol methacrylate (CMP-1E) and acetoxyacetylethyl methacrylate (AAEMA).

5. Shaped body according to claim 3,
wherein the polyfunctional monomer(s) is/are selected from bisphenol A dimethacrylate, 2,2-bis[4-(2-hydroxy-3-methacryloyloxypropyl)phenyl]propane (bis-GMA; an addition product of methacrylic acid and bisphenol A diglycidyl ether), eth-oxy- or propoxylated bisphenol A dimethacrylate, 2-[4-(2-methacryloyloxy-ethoxy-ethoxy)phenyl]-2-[4-(2-methacryloyloxy-ethoxy)phenyl]propane), 2,2-bis[4-(2-meth-acryloxy-propoxy)phenyl]propane, 1,6-bis-[2-methacryloyloxyethoxycarbonylamino]-2,2,4-trimethylhexane (UDMA; an addition product of 2-hydroxyethyl methacrylate and 2,2,4-trimethylhexamethylene diisocyanate), TMX-UDMA (an addition product of a mixture of HEMA and hydroxypropyl methacrylate (HPMA) with α,α,α', α'-tetramethyl-m-xylylene diisocyanate (TMXDI)), di-, tri- or tetraethylene glycol dimethacrylate, trimethylolpropane trimethacrylate, pentaerythritol tetramethacrylate, glycerol di- or trimethacrylate, 1,4-butanediol dimethacrylate, 1,10-decanediol dimethacrylate (D3MA), 1,12-dodecanediol dimethacrylate and bis(3-methacryloyloxymethyl)tricyclo-[5.2.1.0$^{2,6}$]decane (DCP).

6. Shaped body according to claim 3,
wherein the polymeric resin matrix is formed by polymerization of a mixture of
methyl methacrylate,
at least one of UDMA and TMX-UDMA, and
ethylene glycol dimethacrylate.

7. Shaped body according to claim 1,
wherein the organic filler has a lower opacity than the resin matrix.

8. Shaped body according to claim 1,
wherein the thickener has an average particle size of from 10 to 60 μm and the at least one organic filler has an average particle size of from 20 to 60 μm.

9. Process of manufacturing the monochromatic shaped body of claim 1 for use as a blank for the production of dental restorations, which comprises curing the following mixture:
(1) 1 to 20 wt.-% polyfunctional radically polymerizable monomer(s),
(2) 10 to 60 wt.-% monofunctional radically polymerizable monomer(s),
(3) 0.01 to 5.0 wt.-% initiator for the radical polymerization,
(4) 20 to 70 wt.-% thickener comprising uncrosslinked polymer particles,
(5) 5 to 50 wt.-% organic filler comprising crosslinked polymer particles having an average particle size (d50 value) of from 20 to 100 μm, and optionally
(6) 0.1 to 5.0 wt.-% further additive(s), in each case relative to the total mass of the mixture, wherein the mixture does not contain inorganic filler and organic-inorganic filler (composite filler).

10. Process according to claim 9, which comprises curing the following mixture:
(1) 2 to 10 wt.-% polyfunctional radically polymerizable monomer(s),
(2) 5 to 50 wt.-% monofunctional radically polymerizable monomer(s),
(3) 0.1 to 3.0 wt.-% initiator for the radical polymerization, (4) 30 to 60 wt.-% thickener,
(5) 10 to 40 wt.-% organic filler and optionally
(6) 0.1 to 2.0 wt.-% further additive(s), in each case relative to the total mass of the mixture.

11. Process according to claim 9, which comprises curing the following mixture:
   (1) 3 to 8 wt.-% polyfunctional radically polymerizable monomer(s),
   (2) 10 to 45 wt.-% monofunctional radically polymerizable monomer(s),
   (3) 0.1 to 2.0 wt.-% initiator for the radical polymerization,
   (4) 35 to 55 wt.-% thickener,
   (5) 15 to 35 wt.-% organic filler and optionally
   (6) 0.2 to 1.5 wt.-% further additive(s), in each case relative to the total mass of the mixture.

12. Shaped body according to claim 1, further comprising at least one pigment as colorant.

13. Shaped body according to claim 12, which contains 0.0002 to 1.0 wt.-% of at least one pigment, relative to the total mass of the shaped body.

14. Process of using the shaped body according to claim 1 for the production of artificial teeth or tooth segments.

15. Process according to claim 14, wherein the artificial teeth or the tooth segments are produced by a cutting process.

16. Process according to claim 15, wherein the artificial teeth or the tooth segments are produced by a CAD/CAM process.

17. Process for the production of a shaped body according to claim 1, wherein
   (a) a polymerizable mixture is provided, which contains radically and/or cationically polymerizable resin, the organic filler, the thickener and initiator for the radical and/or cationic polymerization,
   (b) the mixture is coloured by the addition of colorants,
   (c) the opacity of the mixture is optionally adjusted by the addition of pigment(s), and
   (d) the mixture is shaped to form a shaped body and
   (e) cured by radical and/or cationic polymerization.

18. Process according to claim 17, wherein, in step (c), the opacity is adjusted by addition of $TiO_2$ white.

19. Process according to claim 17, wherein the shaped body is shaped in step (d) by introducing the mixture into a casting mould by injection moulding followed by curing.

20. Process of manufacturing the monochromatic dental shaped body of claim 1 for use as a blank for the production of dental restorations, which comprises curing the following mixture:
   (1) 15 to 70 wt.-% mono- and/or polyfunctional radically polymerizable monomer(s),
   (2) 0.01 to 5.0 wt.-% photoinitiator for the radical, cationic or combined polymerization,
   (3) 5 to 90 wt.-% organic filler(s) comprising crosslinked polymer particles having an average particle size (d50 value) of from 20 to 100 μm,
   (4) a thickener comprising uncrosslinked polymer particles and optionally
   (5) 0.1 to 5.0 wt.-% further additive(s), in each case relative to the total mass of the mixture, wherein the mixture does not contain inorganic filler and organic-inorganic filler (composite filler).

21. Process of manufacturing a dental restoration, comprising:
   producing the monochromatic dental shaped body of claim 1 having the form of a blank for the production of a dental restoration, and
   shaping the blank to a dental restoration by a cutting process.

* * * * *